United States Patent
Gilbert et al.

(12) 
(10) Patent No.: US 6,968,728 B2
(45) Date of Patent: Nov. 29, 2005

(54) TEST TAP ADAPTER FOR EXTRACTING DISSOLVED GASES FROM INSULATING OIL AND MEASURING ELECTRICAL PARAMETERS OF A TRANSFORMER BUSHING

(75) Inventors: Roland Gilbert, Dunham (CA); Jocelyn Jalbert, Repentigny (CA); Hong Phuong Nguyen, Montréal (CA); René J. Demers, Beloeil (CA)

(73) Assignee: Hydro Quebec, Quebec (CA)

( * ) Notice: Subject to any disclaimer, the term of this patent is extended or adjusted under 35 U.S.C. 154(b) by 233 days.

(21) Appl. No.: 10/615,930

(22) Filed: Jul. 10, 2003

(65) Prior Publication Data

US 2005/0005674 A1 Jan. 13, 2005

(51) Int. Cl.⁷ ................................................ G01N 1/22
(52) U.S. Cl. ...................... 73/19.12; 73/19.12; 324/126; 324/127; 340/870.18
(58) Field of Search ......................... 73/19.12; 324/126, 324/127; 340/870.18

(56) References Cited

U.S. PATENT DOCUMENTS

| | | | |
|---|---|---|---|
| 3,009,124 A | * 11/1961 | Narbut | 336/57 |
| 3,866,460 A | * 2/1975 | Pearce, Jr. | 73/19.05 |
| 4,112,737 A | 9/1978 | Morgan | |
| 4,757,263 A | * 7/1988 | Cummings et al. | 324/552 |
| 4,763,514 A | 8/1988 | Naito et al. | |
| 5,400,641 A | 3/1995 | Slemon et al. | |
| 5,640,154 A | * 6/1997 | Meyer et al. | 340/870.18 |
| 5,659,126 A | 8/1997 | Farber | |
| 5,749,942 A | 5/1998 | Mattis et al. | |
| 5,830,261 A | 11/1998 | Hamasaki et al. | |
| 6,037,592 A | 3/2000 | Sunshine et al. | |
| 6,391,096 B1 | 5/2002 | Waters et al. | |
| 2003/0160602 A1 | * 8/2003 | Anand et al. | 324/126 |

FOREIGN PATENT DOCUMENTS

WO    WO 9816841 A1   * 4/1998    ........... G01R/31/12

* cited by examiner

*Primary Examiner*—Hezron Williams
*Assistant Examiner*—André K. Jackson

(57) ABSTRACT

The present invention relates to an apparatus for measuring the capacitance and the dissipation factor in a transformer bushing and extracting gas dissolved in the insulating fluid of said bushing. The apparatus comprises a porous cylindrical member associated with a tap connector and covered by a thin layer of a gas permeable but liquid impermeable membrane. The porous member allows passive diffusion of the permeated gas extracted from the insulating fluid of a transformer bushing to a gas storage chamber for further analysis, thereby helping to prevent high costs related to damage or destruction of the bushing.

17 Claims, 8 Drawing Sheets

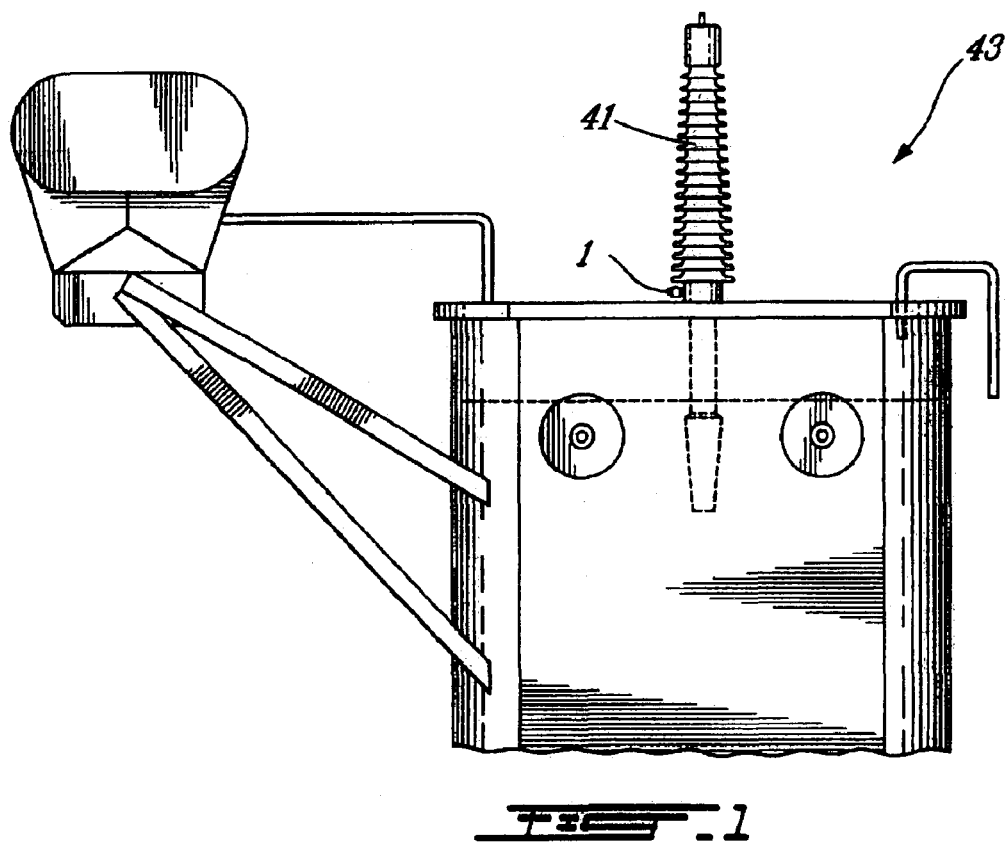

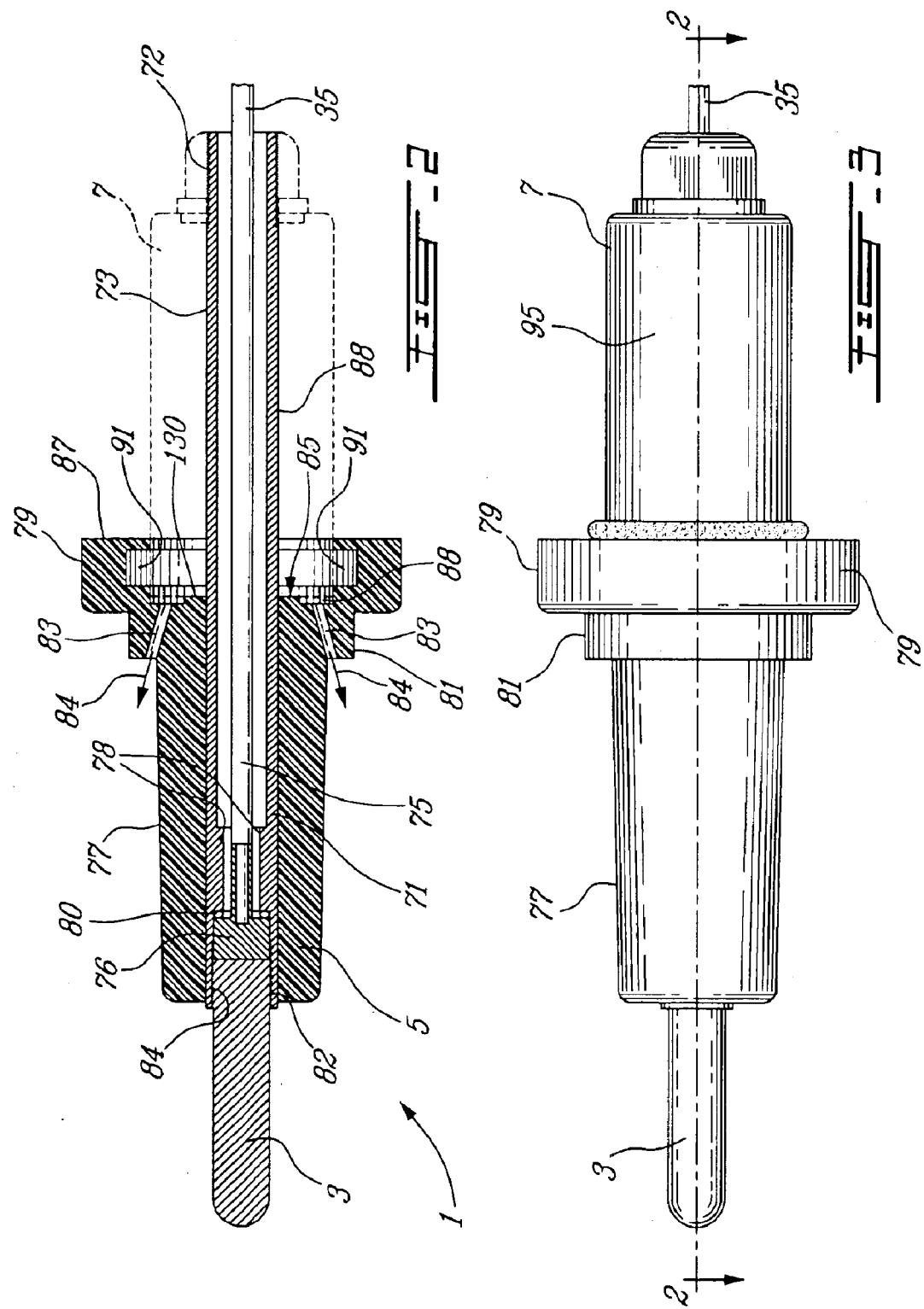

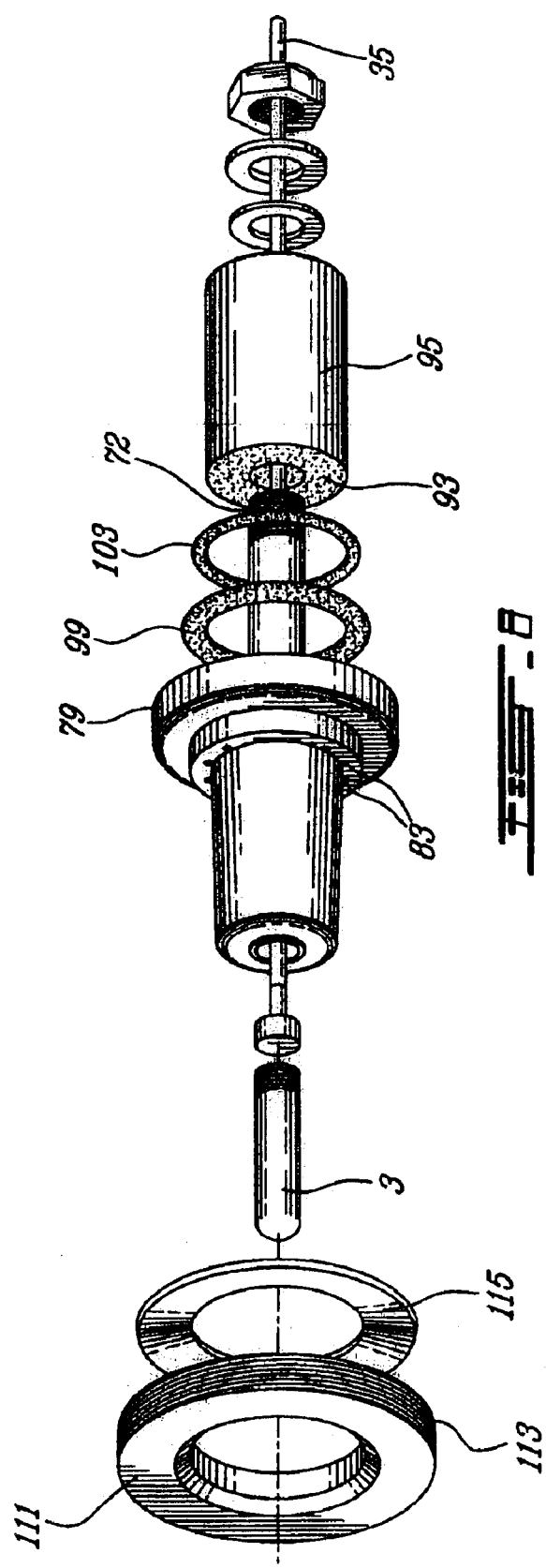

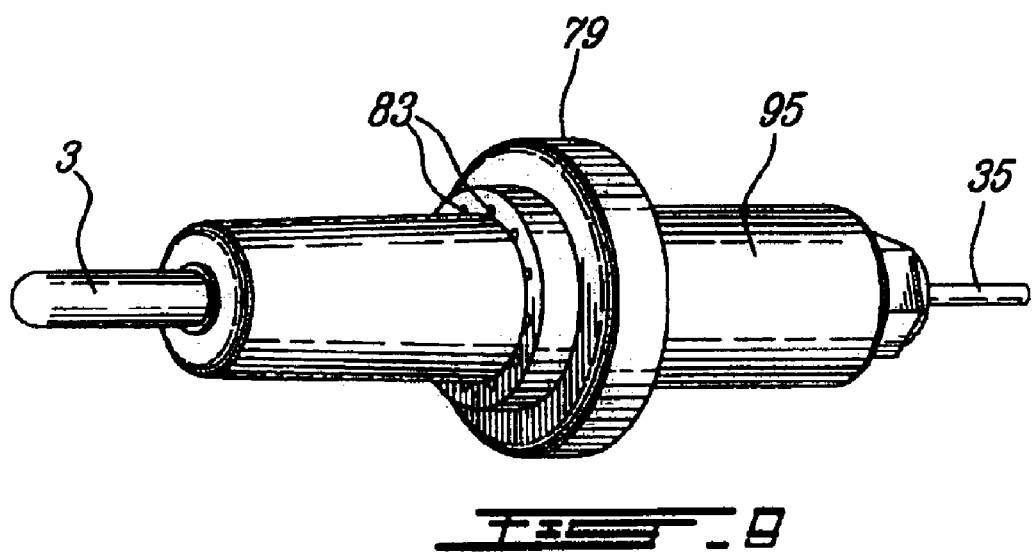

TEST TAP ADAPTER FOR EXTRACTING DISSOLVED GASES FROM INSULATING OIL AND MEASURING ELECTRICAL PARAMETERS OF A TRANSFORMER BUSHING

BACKGROUND OF THE INVENTION (a) Field of the Invention

The present invention relates to a test tap adapter that is designed to be mounted on a bushing of an electrical transformer and is adapted to extract samples of gases dissolved in the insulating oil that is present in the bushing of the transformer. More specifically, the invention is concerned with a test tap that is normally used to make electrical measurements, such as capacitance and dissipation factor, and that is modified to extract samples of gases that may be dissolved within the oil of the bushing whereby the gases that have been extracted may then be analyzed qualitatively and quantitatively to determine the presence of fault-gases therein. In particular, the modified test tap according to the invention is arranged to permit a passive diffusion of dissolved gases that are extracted from the insulating oil, towards a gas storage chamber for further analysis.

(b) Description of Prior Art

In a high-voltage transformer, malfunctions such as electrical arcs, overheating, corona and partial discharges that imply the paper-oil insulation material, lead to the formation of hydrogen, carbon oxides and low molecular weight hydrocarbons such as methane, ethane, acetylene and other gases. The amount of each gas in the oil is therefore indicative of the nature of the problem and consequently, this information is used by the electrical utilities for the diagnosis of the incipient faults. In addition, these compounds are highly volatile and their accumulation within the transformer can lead to an accelerated degradation of the transformer, and in some cases to an explosion of the device. The early detection of the presence of such gases within the insulating oil (i.e. $H_2$, $CO$, $CO_2$, $CH_4$, $C_2H_2$, $C_2H_4$, $C_2H_6$ and $C_3H_8$) in a preventive maintenance action allows electrical utilities to avoid important expenses, especially if they are involved in long distance transport of electricity where some transformers have to be dismantled for repair or simply have to be replaced because of serious damages thereto. It is well known that such fault gases could similarly be produced from the degradation of the insulating material of a high-voltage bushing, which is also a piece of equipment susceptible to some electrical and thermal malfunctions. Although the monitoring of fault gases in the transformers is a worldwide common action, nothing is done at the present time for following their evolution in a bushing mainly because of a total absence of available procedure and device.

The current procedure to establish the presence of fault gases within a transformer is based on a manual sampling of the insulating oil by using a gas-tight syringe. The oil sample is thereafter sent to a laboratory for further analysis. An annual or bi-annual sampling of few milliliters of insulating oil within the large oil tank of the transformer does not modify the insulating conditions of the equipment in use. Sampling using this technique is performed without de-energizing the transformer and has been an important aspect of the preventive maintenance of this electrical equipment for the last three decades. Numerous systems have been also designed with a view to monitoring the presence and the amount of fault gases in the insulating fluid thereby avoiding the need for manual sampling of the oil. Some of these systems include a gas extractor that is directly immersed within the insulating fluid contained in the tanks. In other systems, the gas extractor is in contact with the insulating oil by means of fluid lines. In both approaches, a nonporous membrane is used for extracting the gas that is dissolved in the insulating oil, the gas being stored in a collecting chamber. These gases can further be submitted to a partial or total on site analysis by using well known devices. Generally, the fluid lines are connected to the same inlets on the transformer tank as those used for a manual sampling of the oil. These systems can be used while the electrical equipment is in function.

U.S. Pat. No. 6,391,096 B1 relates to an apparatus and a method for extracting fault gases dissolved in the transformer oil. The apparatus comprises a tubular membrane extractor column connected externally to an oil field electrical component. Particularly, this apparatus uses an extraction module comprising numerous hollow fibers made from a composite material such as polypropylene, polyvinylidene fluoride or polysulfone coupled to a nonporous copolymer. such as perfluoro-2,2-dimethyl-1,3-dioxole with variable amounts of polytetrafluoroethylene. This equipment is strictly for use with high-voltage transformers.

U.S. Pat. No. 6,037,592 relates to a method and an apparatus to monitor and measure the concentration of gases in a gas-containing liquid such as transformer oil. A passive gas extracting technique which comprises a high-performance membrane material to extract dissolved gases from the oil and an IR-based sensor to detect gases present are used. The method and apparatus are not adaptable to the bushing of a transformer.

U.S. Pat. No. 5,830,261 relates to an apparatus for de-aeration of liquids. The assembly includes a de-aeration element having a gas channel-forming component enclosed and sealed within an envelope formed of a nonporous fluoro-polymer film and cannot be used to extract gases from the insulating oil of a transformer bushing.

U.S. Pat. No. 5,749,942 describes an apparatus and a method for extracting gases dissolved within a liquid. The liquid is externally pumped from a reservoir, such as a transformer, to a separation cell. This separation cell is made from a membrane, for example a copolymer of perfluoro-2,2-dimethyl-1,3-dioxole, that is selectively permeable to gas. The membrane is held by a support made of porous materials, for example vinylidene difluororide homopolymer or copolymer to form a composite membrane having improved ruggedness. The separation cell has a tubular shape made of concentric or spiral circles. This system cannot be used with a transformer bushing, while the transformer is in operation.

U.S. Pat. No. 5,659,126 describes the use of a gas chromatograph to measure the concentration of fault gases comprised within the headspace of a transformer, referred to as the cover gas at the top of the transformer. A sample of gas is removed automatically and periodically from the transformer and transferred directly to a gas chromatograph for further analysis. It will be realized that this system cannot be mounted in permanence in the bushing of a transformer.

U.S. Pat. No. 5,400,641 describes an apparatus designed to extract the gas dissolved within the oil of electrical transformers and to identify these gases and their respective concentrations. Particularly, the oil from the transformer circulates through an external extraction chamber, which is maintained under partial vacuum. The oil is led to the gas extraction chamber through a fluid line and is returned to the transformer while extracted gases are directed to an analysis chamber.

U.S. Pat. No. 4,763,514 relates to an apparatus for measuring the dissolved gas contained within the insulating oil of an electrical equipment. This apparatus comprises a sampling device connected to a tank for sampling a portion of the insulating oil from the electrical equipment, an extracting device connected to the sampling device based on pressure reduction for extracting a volume of dissolved gases from the portion of the insulating oil, and a measuring device connected to the extracting device for measuring the components of the dissolved gas. The portion of oil from which the gas is extracted is further returned to the tank after analysis. This system cannot be mounted in permanence in the bushing of a transformer.

U.S. Pat. No. 4,112,737 describes a gas extractor formed with a plurality of elongated capillary tubes made of polytetrafluoroethylene that are permeable to gases but impermeable to liquids. Each end of the capillary tubes is fixed to a respective manifold which is connected via some extension leads to a test station located at the ground level of the equipment. The extracted gases can be removed from the test station for determining the presence of fault gases.

It will be realized that none of the above art teaches the monitoring of the insulating oil present in the bushing of a transformer.

Although some of the art reports the use of technology allowing passive extraction of gas contained within the insulating fluid of a transformer tank through a selective permeable membrane or vacuum extraction, these techniques cannot be used to monitor the fault gases produced within the transformer bushings since the latter are made of distinct reservoirs that do not communicate with the transformer tanks. Moreover, these devices could not be installed onto transformer bushings without major innovations since for the existing bushings, there is no available opening at the base for inserting such devices. In addition, because the volume of insulating fluid found in the bushings is quite smaller than in a transformer tank, the sampling would be difficult to perform without altering the paper-oil insulating conditions of this piece of equipment.

Actually, the only way to monitor the presence of fault gases within transformer bushings is the sampling of gases in the headspace of the bushing (referring to the cover gas at the top of the bushing) using a gas-tight syringe followed by an analysis of the multicomponent gas sample in a laboratory or on site, using portable equipment such as a gas chromatograph. This is made possible because the fault gases present in the oil are equilibrated in the headspace of the bushing by a principle governed by the Henry's Law, in the same manner as the fault gases present in the oil of a transformer equilibrate in the cover gas of the transformer tank where patented devices could be used to collect samples (i.e. U.S. Pat. No. 5,659,126). One of the major problem of this method is that the transformer unit must be de-energized to allow the staff to reach the opening located at the head of the bushing. One of the functionality of a bushing is to isolate the high-voltage line fixed at its head to the grounded top of the transformer tank to which it is fixed at the base. It is therefore impossible to collect sample without de-energizing the transformer unit, and, by analogy to what is done for the transformer tank, neither is it possible to collect samples in the headspace of the bushing using collecting lines that lead the sample to a collecting station located at the base of the transformer unit. Sampling of oil through the bushing head opening by inserting collecting tubes could be also envisaged, however, this could not be done, again without de-energizing the transformer unit. Moreover, any sample collection passing by the headspace of a bushing could lead to undesired contamination of the device by infiltration of solid particles and air humidity, and besides, could represent a higher risk for the maintenance staff considering that the device could be overpressurized. These approaches are consequently strictly reserved to the most problematic cases.

Therefore, there is a need for a convenient and affordable way to monitor the fault gases generated by incipient faults in the bushing of a transformer unit while keeping this apparatus functional and without altering the insulating conditions of the bushing.

SUMMARY OF THE INVENTION

It is an object of the present invention to provide a test tap adapter capable of extracting and determining samples of gas in the insulating oil of the bushing of a transformer.

It is another object of the present invention to provide a device that contributes to save costs in repairing or replacing damaged high-voltage transformers.

The above and other objects of the invention may be achieved by providing a test tap adapter for use in providing electrical measurements in a transformer bushing and arranged for extracting samples of gases dissolved in insulating oil present in the transformer bushing so as to qualify and quantify the presence of fault gases in the insulating oil. The modified test tap adapter includes a tap connector, a tubular runway axially disposed in the tap connector, and having a portion extending outside the tap connector that is constructed to penetrate into the transformer bushing and to soak in the insulating oil. An insulated conductor, for example a twisted-wire conductor, is mounted in the tubular runway along the entire length thereof and has a free length for connection to a conductor provided in the core of the transformer bushing. Means are provided for connecting an end of the insulated conductor opposite its free length, to an electrical measurement means, and there are also means for anchoring the test tap adapter to the transformer bushing through an opening provided therein, with the outside portion of the tubular runway inside the transformer bushing in contact with the insulating oil. The modified test tap adapter is characterized in that it additionally comprises a gas diffusing, porous member mounted over the outside portion of the tubular runway, gas permeable but liquid impermeable means covering the gas diffusing porous member and arranged to allow passage of gases that may be present in the insulating oil towards the gas diffusing porous member, a gas reservoir linked to the tap connector in operative contact with the gas diffusing porous member and means to allow passive diffusion of permeated gases in the gas diffusing porous member towards the gas reservoir for determining the presence of gases in the insulating oil.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 is a perspective view showing the general structure of a transformer with its bushing having a modified test tap according to the invention mounted thereon;

FIG. 2 is a longitudinal cross-section view of the modified test tap according to the invention;

FIG. 3 is a lateral view of the modified test tap according to the invention;

FIG. 8 is another exploded lateral view of the modified test tap according to the invention; and FIG. 9 is lateral view in perspective of the modified test tap according to the invention.

DESCRIPTION OF PREFERRED EMBODIMENT

Figure 4:
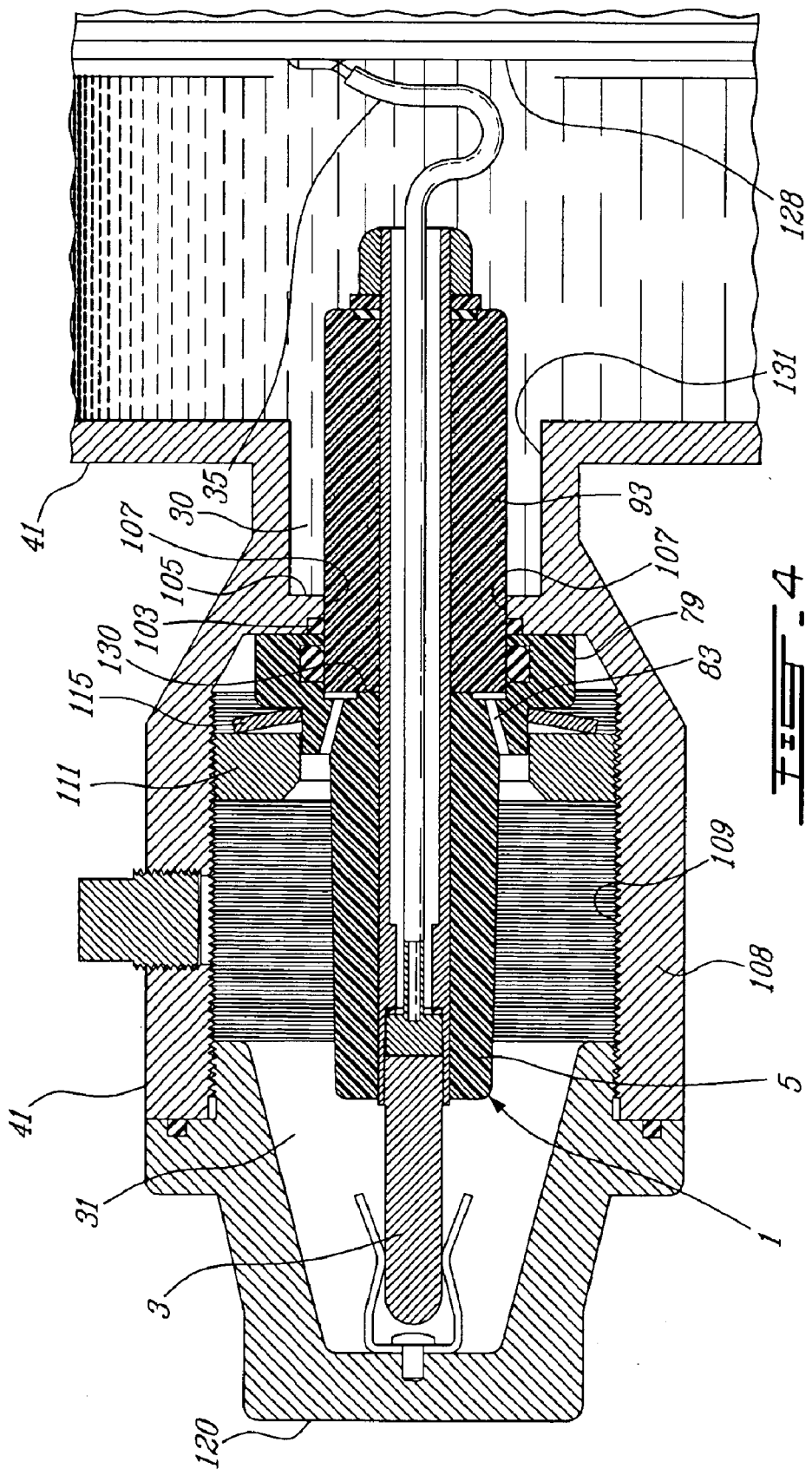
FIG. 4 is a cross-section view of the modified test tap according to the invention fixed in the wall of a transformer bushing.

It will be noted that throughout the annexed drawings, like features are identified by like reference numerals.

Referring to FIG. 1, it will be seen that a modified test tap adapter 1 according to the invention is mounted in known manner on bushing 41 of a conventional transformer 43. It is indeed well known to use a test tap adapter with the bushing of a transformer. However, this type of test tap is restricted for use in making electrical measurements such as capacitance and dissipation factor. It is understood, however, that the test tap adapter according to the invention is somewhat similar in appearance and is similarly mounted in the bushing of a transformer.

Referring now more particularly to FIGS. 2 and 3, it will be seen that modified test tap adapter 1 generally comprises a tap connector 5 in the form of a hollow cylindrical body that is closed at its forward end by means of a gas extractor 7, of which a detailed description will be given later, and at its rear end by means of a metal rod 3 that is also used for connection to an electrical meter (not shown in the drawings) to be used for measuring bushing capacitance for example. An opening 131 is formed in bushing 41 from which a cylindrical casing 108 that is integral with bushing 41 outwardly extends as shown particularly in FIG. 4. On one hand, this casing 108 defines an oil chamber 30 in which the inner end of gas extractor 7 is immersed with the forward end soaking in the main oil volume of the bushing, and on the other hand, a fault-gas storage chamber 31. In other words, for the purpose of the present invention as illustrated particularly in FIG. 4, gas extractor 7 that will be defined in more detail later should partly soak in the oil of bushing 41, here in oil chamber 30 (although oil chamber 30 could be completely eliminated in which case that portion of gas extractor will be exclusively in the oil inside bushing 41, it being further understood that oil chamber 30 is provided for design purpose only). Also as shown, it will be realized that casing 108 extends sufficiently outwardly to enclose the entire length of tap connector 5. Casing 108 is closed by means of tap cover 120 that is screwed thereon thereby defining a sealed fault-gas storage chamber 31. Of course other means could be provided to store the fault gases before analysis as will be appreciated by one skilled in the art.

Tap connector 5, being a cylindrical body of nonconductive material (of a composition well known to those skilled in the art) of a specific shape that will be described more in detail later, has a tubular runway 71 axially disposed along its entire length with a portion 73 extending a certain distance past the forward end of tap connector 5 as particularly shown in FIG. 2 of the drawings. An insulated twisted-wire conductor 75 is disposed in known manner inside tubular runway 71 along the entire length thereof, including portion 73, and has a free length 35 that extends past the forward end of tubular runway 71 for connection to a connector 128 located in the core of bushing 41. So, for taking electrical measurements, connection to the electrical meter mentioned previously is made possible through insulated twisted-wire conductor 75, and metal rod 3 that is in turn electrically connected to the electrical meter (not shown in the drawings).

Referring again to FIG. 2, it will be seen that twisted wire conductor 75 is rearwardly formed with a circular metal plug 76 that is made of a conductive metal and is integral with or otherwise electrically associated with conductor 75. To properly mount conductor 75 inside tubular runway 71 and in electrical contact with metal rod 3, tubular runway 71 is formed with an integral inward collar 78, that extends a short distance and terminates just short of circular metal plug 76. Between the inner face of metal plug 76 and the rearward end of collar 78 enough space is provided to dispose therein an O-ring 80. Finally, as particularly shown in FIG. 2, the rearward end of tubular runway 71 is interiorly threaded at 82, and the forward end of metal rod 3 is outwardly threaded at 84 so that metal rod 3 can be threadedly engaged with tubular runway 71, as shown, via meshing threads 82 and 84. So, for electrically connecting conductor 75 with metal rod 3, O-ring 80 is first disposed against the rearward shoulder of collar 78, then the twisted-wire conductor is introduced, free length 35 first, at the rearward end of tubular runway 71 until circular metal plug 76 abuts O-ring 80. Then, metal rod 3 is screwed at the rearward end of tubular runway 71 until it rests firmly against circular plug 76 and presses the latter against O-ring 80, thereby providing a rigid assembly.

Figure 5:
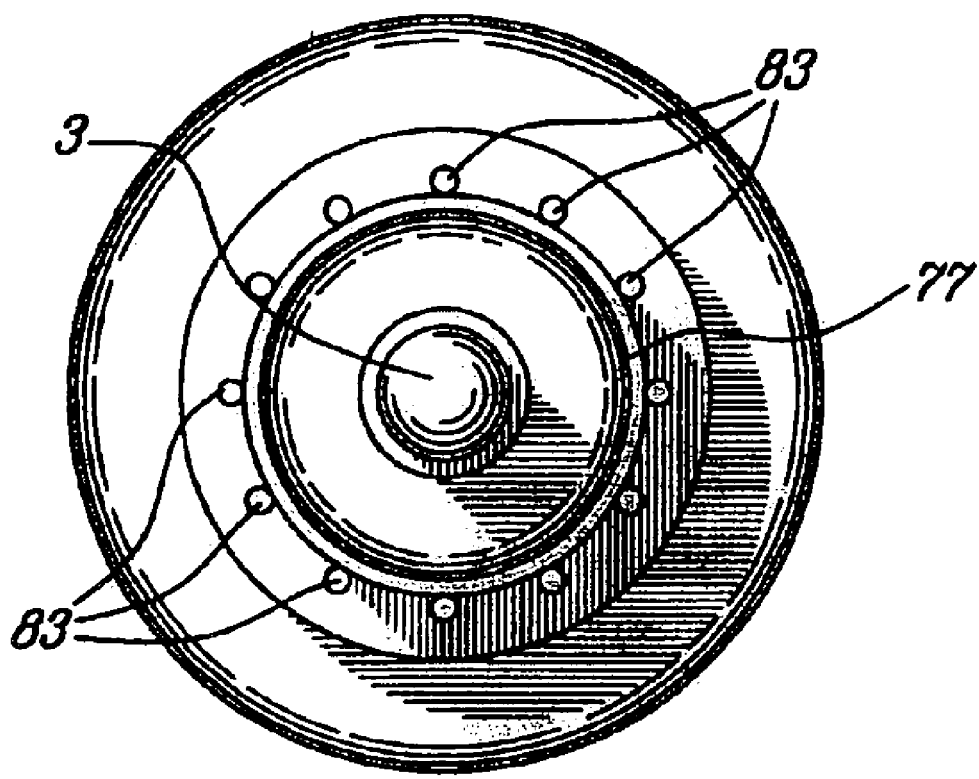
FIG. 5 is a front view of the modified test tap according to the invention.

Tap connector 5 is in the form of a slightly truncated cylinder 77, as particularly shown in FIGS. 2 and 3, and is terminated by a disc like circular flange 79. Between the truncated cylindrical portion 77 and flange 79, there is a circular step member 81 that is better shown in FIG. 3. Step member 81 is essential in this embodiment and has been designed so as to provide a plurality (here twelve although this number can decrease or increase to a large extent depending on circumstances and expected results) of ports 83 of 1 mm diameter or less that extend throughout the entire thickness of circular step member and are regularly distributed around the axis of truncated cylinder 77 (FIG. 5). As seen in FIG. 4, these ports are outwardly flaring in the direction of circulation of the gases towards storage chamber 31, so as to permit an effective passive diffusion of the permeated gases all the way to storage chamber 31 as indicated by arrows 84 (see FIG. 2). These ports must also be in communication with the inner end of gas extractor 7 where the permeated gases exit therefrom. A step 130 provided at the forward end of truncated cylinder 77 defines a circular void 88 that enables porous member 93 to communicate with the totality of ports 83, therefore increasing diffusion surface.

Figure 6:
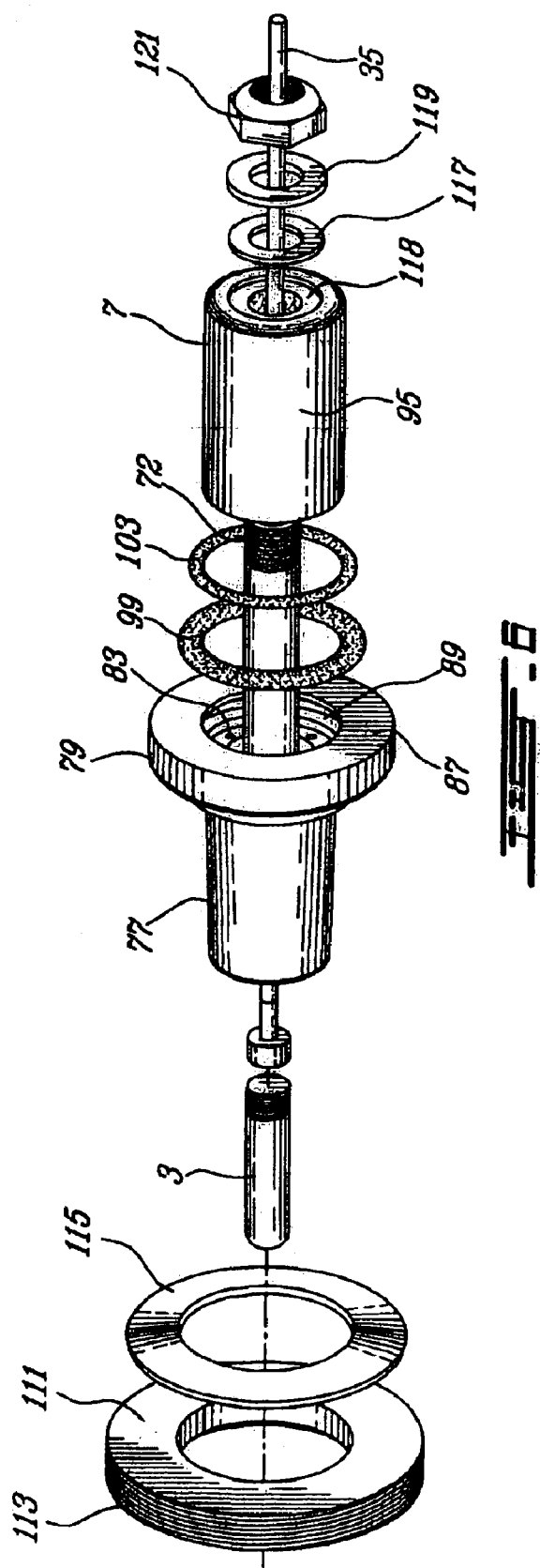
FIG. 6 is an exploded lateral view of the modified test tap according to the invention.

With respect to tap connector 5, particularly flange 79, it will also be seen that the latter extends past the end 85 (see FIG. 2) of truncated cylindrical portion 77, in the form of a crown 87 as seen in FIG. 6, to define a short circular housing 89 adapted to receive the inner end of gas extractor 7 as will be described in detail later. All around the inner face of sleeve 89, a channel 91 has been formed to receive an O-ring 99 as will be described later.

Figure 7:
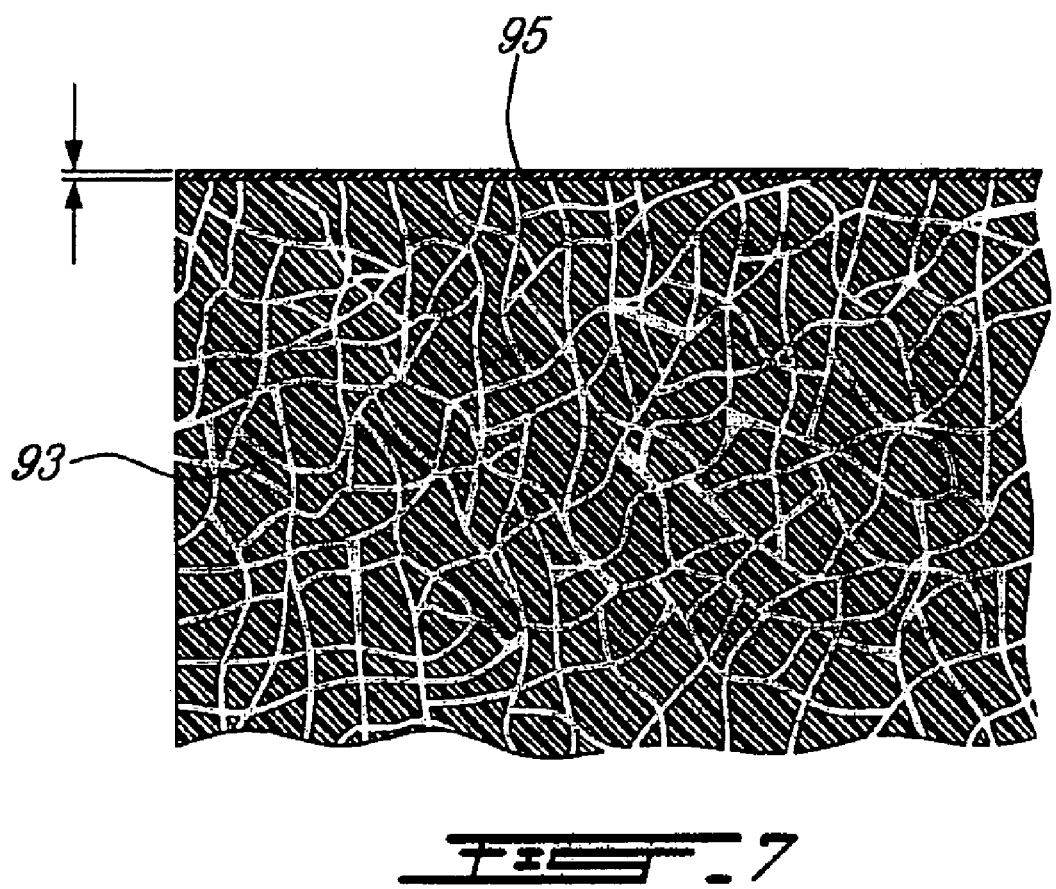
FIG. 7 is a longitudinal cross-section view of part of the gas extractor portion of the modified test tap according to the invention.

Turning now to gas extractor 7, this part of the modified test tap adapter will now be described in detail. It will first be seen that tubular runway 71 has been extended in length to be longer than what is normally found in a standard test tap. This extension of tubular runway is referred to as portion 73, whose length depends upon the clearance available between the solid core and the wall of the bushing 41. Essentially, gas extractor 7 consists of a length of a tubular shaped porous member 93 that is shaped to be mounted over tubular runway 71 to cover the entire portion 73 thereof (FIG. 2). Porous member 93 can be fabricated of any suitable nonconductive material that allows diffusion of gases therethrough. These materials are well known to those skilled in the art, however, in the present embodiment, the preferred material is ultra-high molecular weight polyethylene (PE UHMW) or polyvinylidene fluoride (PVDF) having a porosity of 20 microns and a minimum of 40% pores in volume. This porous member 93 is entirely covered with a thin layer 95 of a gas permeable but liquid impermeable material in membrane form (FIG. 7). This type of material is well known to those skilled in the art, however, for the present embodiment of the invention, the preferred material is a nonporous copolymer of perfluoro-2,2-dimethyl-1,3-dioxole (PDD) and tetrafluoroethylene TFE of thickness between 20 and 120 microns (PDD-TFE copolymer). Other fluorine containing monomers copolymerized with PDD may also be used such as vinylidene fluoride, chlorotrifluoroethylene, vinyl fluoride, and perfluoromethyl vinyl ether.

Before describing gas extractor 7 still more in detail, it should be noted that the forward end of tubular runway 71 is threaded at 72 (as indicated in FIG. 6). Porous member 93, completely covered as indicated above with layer 95 is slid over the tubular runaway 71 on portion 73 until the inner end abuts end face 85 of truncated cylindrical portion 77 and fits into circular housing 89. Before engaging the inner end of porous member 93 into circular housing 89, an O-ring 99 has been inserted into channel 91 to prevent any escape of permeated gas except through outwardly flaring ports 83.

Once the porous member is in place within circular housing 89, an O-ring 103 is mounted as shown around porous member 93 and tight against the face of crown 87, thereby preventing any entry of oil from oil chamber 30 to gas collecting chamber 31 when porous member 93 soaks therein.

Before describing how the modified test tap adapter is mounted in bushing 41, it will be noted that opening 131 provided in the wall of bushing 41 to form an oil chamber 30 is in the shape of a cylindrical recess that terminates into an abutting wall 105, the latter being formed with a circular opening 107 shaped to permit passage of gas extractor 7 therethrough. In addition, cylindrical casing 108 is threaded at 109 for the reason that will now be explained (see FIG. 4).

To complete the assembly of the modified test tap adapter according to the present embodiment, there is additionally provided a circular tightening screw 111 that is threaded at 113 on its outer periphery (FIG. 6) and that is engageable with threads 109. In addition, a spring disc 115 is disposed between circular tightening screw 111 and flange 79. Gas extractor 7 is completed by providing a seal 117 which is disposed in a ring like cavity 118 formed at the outer end of porous member 93 covered with membrane 95, a Teflon washer 119 facing seal 117 and a locking nut 121 that is engaged in thread 72 at the end of tubular runway 71 (see FIG. 6).

So, for installing modified test tap adapter 1 in the wall of bushing 41, it is first introduced into fault gas storage chamber 31, then partially into chamber 30 for fixing free length 35 of the insulated twisted-wire conductor 75 to conductor 108 located in the core of bushing 41. Then, the gas extractor 7 is completely pushed through opening 107 formed in abutting wall 105, into the interior of bushing 41, until flange 79 comes to rest firmly against abutting wall 105. Then, spring disc 115 is placed against the inner face of flange 79 and circular tightening screw 111 is screwed into threads 109 of fault gas storage chamber 31. When bushing 41 is afterwards filled with insulating oil, gas extractor 7 is then soaking in the oil from which the fault gases are extracted by permeation through membrane 95 covering porous member 93.

As it is well know to those skilled in the art, this test tap adapter can be used to make normal electrical measurements through insulated twisted-wire conductor 75 and oil soaking free length 35 thereof. However, in accordance with the present invention, all the time the test tap is unoperated for electrical measurements, any fault gas will be extracted from the insulating oil through membrane 95, porous member 93 and because of the passive diffusion arrangement of the test tap, particularly the diffuser formed by ports 83, all these gases will equilibrate in fault gas storage chamber 31. Besides monitoring the problems that could occur in a bushing, the use of fault-gas storage chamber 31 will also enable detection of an inadequate electrical contact between metal rod 3 and test tap cover 120 (see FIG. 4). It is not possible to have access to this information by simply analyzing the gas in the headspace of a bushing. Storage chamber 31 could be connected to an external collect station via connecting gas lines as known to those skilled in the art. The multicomponent gas equilibrated in storage chamber 31 could then be extracted from this station with a syringe for laboratory analysis or, alternatively, led to a gas chromatograph directly connected to the collect station, while keeping this transformer unit functional (i.e. U.S. Pat. No. 4,112, 737). The multicomponent gas could also be analyzed by the means of gas sensors that could be directly installed inside fault-gas storage chamber 31, or by any other means.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

We claim:

1. A test tap adapter for use in providing electrical measurements in a transformer bushing and arranged for extracting samples of gases dissolved in insulating oil present in said transformer bushing so as to determine presence of said gases in said insulating oil, said test tap adapter including a tap connector, a tubular runway axially disposed in said tap connector and having a portion extending outside said tap connector, said portion constructed to penetrate into said transformer bushing and to soak in said insulating oil, an insulated conductor mounted in said tubular runway along entire length thereof and having a free length for connection to a conductor provided in said transformer bushing, means for connecting an end of said insulated conductor opposite said free length to an electrical measurement means, and means for anchoring said test tap adapter to said transformer bushing through an opening provided therein, with said outside portion of said tubular runway inside said transformer bushing in contact with said insulating oil, wherein said test tap adapter additionally comprises a gas diffusing member of nonconductive material mounted over said outside portion of said tubular runway, gas permeable but liquid impermeable means covering said gas diffusing member and arranged to allow permeation of gases that may be present in said insulating oil towards said gas diffusing member, a gas storage chamber linked to said tap connector, in operative contact with said gas diffusing member and means to allow passive diffusion of permeated gases present in said gas diffusing member towards said gas storage chamber for determining the presence of gases in said insulating oil.

2. Test tap adapter according to claim 1, wherein said gas diffusing member is porous.

3. Test tap adapter according to claim 1, wherein said insulated conductor is a twisted-wire conductor.

4. Test tap adapter according to claim 1, wherein said tap connector comprises a longitudinally extending cylindrical member, said tubular runway being mounted in said cylindrical member.

5. Test tap adapter according to claim 2, wherein said gas diffusing porous member is cylindrical and shaped to fit over the outside portion of said tubular runway.

6. Test tap adapter according to claim 5, wherein said gas diffusing porous member is made of a polyethylene nonconductive material.

7. Test tap adapter according to claim 5, wherein the nonconductive material of said gas diffusing porous cylindrical member is made of polyvinylidene fluoride.

8. Test tap adapter according to claim 1, wherein said gas permeable but liquid impermeable means comprises a gas permeable membrane.

9. Test tap adapter according to claim 8, wherein said gas permeable membrane has a thickness between 20 and 120 microns.

10. Test tap adapter according to claim 8, wherein said gas permeable membrane is made of a nonporous polymer material.

11. Test tap adapter according to claim 10, wherein said nonporous polymer material comprises a copolymer.

12. Test tap adapter according to claim 11, wherein said copolymer comprises perfluoro-2,2-dimethyl-1,3-dioxole with variable amounts of tetrafluoroethylene.

13. Test tap adapter according to claim 12, wherein said perfluoro-2,2-dimethyl-1,3-dioxole is copolymirized with other fluorine containing monomers, namely vinylidene fluoride, chlorotrifluoroethylene, vinyl fluoride, and perfluoromethyl vinyl ether.

14. Test tap adapter according to claim 5, wherein said gas diffusing porous cylindrical member has a porosity of 10 to 30 microns.

15. Test tap adapter according to claim 14, wherein pores in said gas diffusing porous cylindrical member represent 30 to 50% of the volume of said gas diffusing cylindrical member.

16. Test tap adapter according to claim 5, wherein said tap connector has a forward end in contact with a rear end of said gas diffusing porous member, said forward end of said tap connector comprising a circular step, at least one flaring port extending from a face of said forward end through said circular step and arranged to communicate with said gas storage chamber.

17. Test tap adapter according to claim 16, which comprises a circular casing projecting from the opening of said transformer bushing and constructed to enclose said tap connector including said tubular runway and said gas diffusing porous member and to define said gas storage chamber, and a test tap cover closing said circular casing and sealing said gas storage chamber.

\* \* \* \* \*